United States Patent [19]

Schloemer et al.

[11] Patent Number: 5,621,140

[45] Date of Patent: Apr. 15, 1997

[54] RESOLUTION OF IBUPROFEN

[75] Inventors: George C. Schloemer, Longmont; Eric Lodewijk; Gregory P. Withers, both of Boulder, all of Colo.

[73] Assignee: Syntex (U.S.A.) Inc., Palo Alto, Calif.

[21] Appl. No.: 361,627

[22] Filed: Dec. 22, 1994

[51] Int. Cl.⁶ .................................................. C07C 55/00
[52] U.S. Cl. ............................................ 562/401; 562/496
[58] Field of Search ................................... 562/401, 402, 562/496

[56] References Cited

U.S. PATENT DOCUMENTS

| | | |
|---|---|---|
| 3,228,831 | 1/1966 | Nicholson et al. . |
| 3,385,886 | 5/1968 | Nicholson et al. . |
| 4,209,638 | 6/1980 | Nicholson et al. . |
| 4,246,164 | 1/1981 | Felder et al. . |
| 4,246,193 | 1/1981 | Holton . |
| 4,501,727 | 2/1985 | Armitage et al. . |
| 4,515,811 | 5/1985 | Holton . |
| 4,851,444 | 7/1989 | Sunshine et al. . |
| 4,983,765 | 1/1991 | Lukas et al. . |
| 4,994,604 | 2/1991 | Tung et al. . |
| 5,015,764 | 5/1991 | Manimaran et al. . |
| 5,100,918 | 3/1992 | Sunshine et al. .............. 514/557 |
| 5,332,834 | 7/1994 | Bhattacharya et al. . |

FOREIGN PATENT DOCUMENTS

| | | |
|---|---|---|
| 0095901 | 12/1983 | European Pat. Off. . |
| 529835A2 | 3/1993 | European Pat. Off. . |
| WO93/14056 | 7/1993 | WIPO . |
| WO93/15040 | 8/1993 | WIPO . |

OTHER PUBLICATIONS

E. Schröder, C. Rufer, R. Schmiechen, "Pharmazeutische Chemie", 1982, Georg Thieme Verlag (Stuttgart, New York), pp. 440–449.

Kaiser, et al., "Isomeric Inversion of Ibuprofen (R)–Enantiomer in Humans", *J. Pharm. Sci.*, 65(2), pp. 269–273 (1976).

*Primary Examiner*—Samuel Barts
*Attorney, Agent, or Firm*—Heller Ehrman White & McAuliffe

[57] ABSTRACT

(S)-ibuprofen may be separated from a mixture of (S)-ibuprofen and (R)-ibuprofen in high yield and enantiomeric purity in a single resolution step using an N-alkyl-D-glucamine as the resolving agent.

19 Claims, No Drawings

RESOLUTION OF IBUPROFEN

BACKGROUND OF THE INVENTION

1. Field of the Invention

This invention relates to the resolution of ibuprofen, in particular to separating (S)-ibuprofen from a mixture of (S)-ibuprofen and (R)-ibuprofen.

2. Description of the Field

Ibuprofen, α-methyl-4-(2-methylpropyl)benzeneacetic acid, is a well-known nonsteroidal anti-inflammatory, antipyretic, and analgesic agent described in U.S. Pat. Nos. 3,228,831 and 3,385,886 (Nicholson et al.) Ibuprofen is predominantly sold commercially as the racemic compound; however, since the (S)-ibuprofen is described as being the more active enantiomer [see, for example, U.S. Pat. No. 4,851,444 (Sunshine et al.)], development of (S)-ibuprofen is well advanced.

Numerous processes for the preparation of (S)-ibuprofen have been disclosed, most related to resolution.

The use of (S)-α-methylbenzylamine as the resolving agent has been described in the patent and non-patent literature. For example, Kaiser et al., J. Pharm. Sci., 65(2), 269–273 (1976), disclose the separation of (S)-ibuprofen from racemic ibuprofen. U.S. Pat. No. 4,209,638 (Nicholson et al.) discloses a process for increasing the proportion of the desired enantiomer from racemic arylpropionic acids (such as ibuprofen) by a partial dissolution resolution technique. U.S. Pat. No. 4,983,765 (Lukas et al.) discloses a separation process in which the reaction to a diastereomeric salt takes place in a polar solvent, and the salt is purified by several crystallizations to produce optically pure material. U.S. Pat. No. 5,015,764 (Manimaran et al.) discloses a process in which the racemic mixture is initially treated with an organic or inorganic base to form a salt solution, and the salt solution is treated with a chiral base such as (S)-α-methylbenzylamine to precipitate the less soluble diastereomeric salt from the reaction solution; and PCT Published Application No. WO 93/15040 (Ethyl Corporation) discloses an improvement to that process where an inorganic or organic salt, soluble in the salt solution of the resolution process, is added to enhance the separation.

The use of other resolving agents has also been described. U.S. Pat. No. 4,994,604 (Tung et al.) discloses the use of (S)-lysine in a preferential crystallization method for the formation of the (S)-ibuprofen (S)-lysine salt; and U.S. Pat. No. 5,332,834 (Bhattacharya et al.) discloses an improvement on that process including the racemization and recycle of the (R)-ibuprofen. Published European Patent Application No. 0529835 (Nagase & Co.) discloses the use of various optically active phenyl substituted amines, such as 2-(4-methylphenyl)-3-methylbutylamine, as resolving agents.

U.S. Pat. No. 4,246,164 (Felder et al.) discloses the use of N-methyl-D-glucamine [1-deoxy-1-(methylamino)-D-glucitol, meglumine], and U.S. Pat. Nos. 4,246,193 and 4,515,811 (Holton) disclose the use of other N-alkyl-D-glucamines, as resolving agents in the preparation of naproxen [(S)-6-methoxy α-methyl-2-naphthaleneacetic acid].

U.S. Pat. No. 4,501,727 (Armitage et al.) discloses the N-methyl-D-glucamine salt of (+)-flurbiprofen [(S)-flurbiprofen]; although it does not disclose N-methyl-D-glucamine as the resolving agent for flurbiprofen.

The disclosures of these and other documents referred to throughout this application are incorporated herein by reference.

SUMMARY OF THE INVENTION

We have discovered that (S)-ibuprofen may be separated from a mixture of (S)-ibuprofen and (R)-ibuprofen in high yield and enantiomeric purity in a single resolution step using an N-alkyl-D-glucamine as the resolving agent.

In one aspect, this invention relates to a process for separating (S)-ibuprofen from a mixture of (S)-ibuprofen and (R)-ibuprofen, comprising using an N-alkyl-D-glucamine as the resolving agent.

In another aspect, this invention relates to (S)-ibuprofen N-alkyl-D-glucamine salts.

This invention provides several advantages and economies:

first, the process produces (S)-ibuprofen of high enantiomeric purity in a single resolution step, avoiding the need for recrystallization;

second, the process produces (S)-ibuprofen in high yield;

third, the process uses an N-alkyl-D-glucamine as an inexpensive resolving agent;

fourth, the process avoids the need for an auxiliary base, although one may be used;

fifth, the process readily permits the recycle of the resolving agent and solvents, and the racemization and recycle of the (R)-ibuprofen-containing residues from the separation; and sixth, the process can readily be adapted to commercial-scale production.

DETAILED DESCRIPTION OF THE INVENTION

Definitions

"Ibuprofen" refers to a mixture of (S)-ibuprofen and (R)-ibuprofen, especially to a racemic mixture. The individual enantiomers are specifically designated as (S)-ibuprofen or (R)-ibuprofen.

"Substantially pure", when referring to the chemical purity of (S)-ibuprofen or its salt with an N-alkyl-D-glucamine, means that the material contains at least 95%, preferably at least 98%, more preferably at least 99% of the named compound. The resolution process of this invention does not generate impurities in the ibuprofen; thus, if commercial ibuprofen is used as the starting material, the resulting (S)-ibuprofen will be of similar purity and thus be substantially pure.

"Substantially enriched", "high enantiomeric purity", and similar terms when referring to the enantiomeric purity of (S)-ibuprofen or its salt with an N-alkyl-D-glucamine, mean that the material has an enantiomeric excess of at least 90%, preferably at least 95%, more preferably at least 98% of the named enantiomer.

"Alkyl" in N-alkyl-D-glucamine refers to a straight chain saturated hydrocarbyl group having from one to eighteen carbon atoms or a branched or cyclic saturated hydrocarbyl group having from three to twelve carbon atoms. Typical alkyl groups include methyl, ethyl, propyl, 2-propyl, cyclopropyl, butyl, 2-butyl, 1,1-dimethylethyl, cyclopropylmethyl, hexyl, cyclohexyl, octyl, dodecyl, octadecyl and the like. The N-alkyl-D-glucamines used as resolving agents in this invention may easily be prepared by literature methods, such as the methods of U.S. Pat. No. 4,246,193; and N-methyl-D-glucamine is commercially available, e.g., from Aldrich. Preferred N-alkyl-D-glucamines are those where the alkyl group has at least six carbon atoms, because the N-alkyl-D-glucamines are then substantially insoluble in water and may be easily recovered from aqueous systems. A particularly preferred N-alkyl-D-glucamine is N-octyl-D-glucamine. The N-alkyl-D-glucamine/(S)-ibuprofen molar ratio used in the resolution process is preferably not substantially greater than 1; typically, increasing the quantity of N-alkyl-D-glucamine used will increase the yield but, beyond a certain point, may lower the enantiomeric purity of the (S)-ibuprofen produced. A suitable N-alkyl-D-glucamine/(S)-ibuprofen molar ratio, when the starting ibuprofen is racemic, is 0.7–1.1, preferably 0.8–1, more preferably 0.9–0.95.

"Inert solvent" refers to solvents of low chemical reactivity with ibuprofen and N-alkyl-D-glucamines. Inert solvents suitable for the process of this invention are those in which the solubility of the (S)-ibuprofen N-alkyl-D-glucamine salt is substantially lower than the solubilities of (S)-ibuprofen and (R)-ibuprofen [or their salts with the auxiliary base, if one is used] and of the (R)-ibuprofen N-alkyl-D-glucamine salt. Suitable inert solvents include both nonpolar solvents, for example aromatic hydrocarbons such as toluene, benzene, and xylene, aliphatic hydrocarbons such as hexane, and the like; or polar solvents, such as alcohols having 1 to 10 carbon atoms, for example, methanol, ethanol, propanol, 2-propanol, or butanol, and ketones having 3 to 10 carbon atoms, for example, acetone or 4-methyl-2-pentanone. The inert solvent used may be, but is not required to be, generally immiscible with water. An "inert solvent" used in the process of this invention may be a single compound or a mixture. A preferred inert solvent is toluene (preferably containing up to 1% water or 10% $C_1$-$C_4$ alcohol, e.g. 2-propanol). While a wide range of inert solvents is suitable for the process of this invention, one of ordinary skill in the art should have no difficulty, having regard to that skill and this disclosure, in finding a suitable inert solvent.

An "auxiliary base" is a base other than the resolving agent which is optionally used in conjunction with the resolving agent and, if present, forms salts with the ibuprofen enantiomers that are soluble in the inert solvent. Auxiliary bases include both inorganic bases, such as alkali metal hydroxides, for example, sodium hydroxide or potassium hydroxide; and organic bases, such as tertiary amines, for example, triethylamine, triethanolamine, and tributylamine. Although many resolution processes require the use of an auxiliary base, it is an advantage of this invention that an auxiliary base is not required, though one may be used if desired. If an auxiliary base is used, the auxiliary base/total ibuprofen molar ratio in the resolution mixture may be up to about 1; more typically, the quantity of auxiliary base will be such that the (N-alkyl-D-glucamine+auxiliary base)/total ibuprofen molar ratio in the resolution mixture will be up to about 1, so that for the resolution of racemic ibuprofen the auxiliary base/(R)-ibuprofen molar ratio will be up to about 1.

Resolution

A mixture of (S)-ibuprofen and (R)-ibuprofen, typically a racemic mixture, and the appropriate quantity of N-alkyl-D-glucamine are heated, with optional agitation, in the inert solvent, generally to a temperature in the range from about 50° to about 100° C. or the reflux temperature of the solvent. The heating is continued until the solids dissolve. Following dissolution of the solids, the solution is slowly cooled to precipitate the desired (S)-ibuprofen N-alkyl-D-glucamine salt. During the cooling process, the solution is preferably seeded with the (S)-ibuprofen N-alkyl-D-glucamine salt. The final temperature to which the solution is cooled is chosen by practical considerations, generally in the range of 0°–40° C., preferably in the range of 10°–20° C., selected so that the difference between the maximum and minimum temperatures will be sufficient to provide a high yield of the salt. The salt/solution mixture may be maintained at the lower temperature until precipitation is complete, or nearly so, usually for about 30 minutes to about several hours. The precipitate that results, a product substantially enriched in the (S)-ibuprofen N-alkyl-D-glucamine salt, is filtered and washed. The filtrate and washings are saved for racemization and recycle of the contained materials.

Separation of (S)-ibuprofen

The separation of the (S)-ibuprofen from the (S)-ibuprofen N-alkyl-D-glucamine salt depends on whether the N-alkyl-D-glucamine is water-soluble.

If the N-alkyl-D-glucamine is water-soluble, the salt is dissolved in water and cleaved with a strong acid, such as hydrochloric acid, to give a precipitated product substantially enriched in (S)-ibuprofen, which is filtered, washed, and dried. Further recrystallization is not generally necessary. The N-alkyl-D-glucamine may be recovered from the filtrate.

If the N-alkyl-D-glucamine is not water-soluble, the salt is dissolved in water and cleaved with a strong base, such as an aqueous alkali metal hydroxide, generally at elevated temperature. The time and temperature of treatment should be chosen to avoid excessive racemization of the (S)-ibuprofen or degradation of the N-alkyl-D-glucamine. The resulting solution is cooled, and the N-alkyl-D-glucamine that precipitates is recovered by filtration, washed, and saved for recycle. The aqueous filtrate from recovery of the N-alkyl-D-glucamine is then processed to obtain (S)-ibuprofen. The filtrate is acidified with a strong acid, such as hydrochloric acid, to give a precipitated product substantially enriched in (S)-ibuprofen, which is filtered, washed, and dried. Further recrystallization is not generally necessary.

Recycle and Racemization

The filtrate and washings from the initial resolution may also be processed for recycle and racemization of the contained materials, (R)-ibuprofen with lesser quantities of (S)-ibuprofen and N-alkyl-D-glucamine, and the solvents. If a water-immiscible inert solvent has been used in the resolution, the solution is first extracted with an aqueous solution of a strong acid, such as hydrochloric acid, and the aqueous and organic phases are separated. The aqueous phase is treated with a strong base, such as an alkali metal hydroxide, to recover the N-alkyl-D-glucamine in the manner described previously. The organic phase, enriched in (R)-ibuprofen, can be racemized. The organic phase is extracted with a basic aqueous solution, such as aqueous sodium hydroxide, and the phases separated. The aqueous phase is heated at about 50°–200° C., preferably at about 100°–150° C., for about 1–20 hours, preferably for about 3–10 hours; cooled; and acidified. The precipitate that results, racemic ibuprofen, is filtered, washed, and dried. The recovered racemic ibuprofen may be recycled into the resolution process.

The solvents used in the resolution process of this invention may be recycled by methods well-known to one of ordinary skill in the art, such as by phase separation, washing, and distillation.

EXAMPLES

The invention is illustrated without limitation by the following Examples, in which:

the yields of (S)-ibuprofen N-alkyl-D-glucamine salt and (S)-ibuprofen are given as percentages of the (S)-ibuprofen content of the starting ibuprofen;

the enantiomeric purity of the (S)-ibuprofen is given as the percentage enantiomeric excess, abbreviated as % ee, [%(S)-ibuprofen—%(R)-ibuprofen]. This was measured by chiral HPLC, using a Whelk-o-1 column, with a mobile phase of hexane/2-propanol/acetic acid (99:1:0.2), elution at 2 mL/min, and detection by UV absorption at 230 nm. Ibuprofen samples were prepared for analysis by dissolving 3–5 mg in 1 mL of the mobile phase; ibuprofen N-alkyl-D-glucamine salt samples were prepared by mixing 15–20 mg in 1N HCl (2 mL) and hexane (3 mL), and injecting a portion of the hexane layer. (S)-ibuprofen eluted at 5 minutes, (R)-ibuprofen at 6 minutes;

melting ranges, MR, are uncorrected; and chemical purities are determined by HPLC. The column used was a Zorbax SB-Phenyl 4.6×150 mm column with 5μ packing, elution at 2 mL/min, and detection by UV absorption at 235 nm. The mobile phase was acetonitrile/water (with 0.03% $H_3PO_4$), 45:55 for the first 5 minutes, changing to 80:20 over the next 3 minutes, 80:20 for 4 minutes, and 45:55 for 4 minutes, for a total cycle of 16 minutes. Ibuprofen samples were prepared for analysis by dissolving 2–3 mg in 1 mL of acetonitrile/water (80:20).

Example 1. Resolution Using N-Octyl-D-glucamine

Racemic ibuprofen (80 g, 390 mmol), toluene (200 mL), and water (0.5 mL) were stirred at 40° C., and N-octyl-D-glucamine (53.8 g, 183 mmol, N-octyl-D-glucamine/(S)-ibuprofen molar ratio=0.938) was added to the solution. The resulting thick slurry was heated to 78° C., forming a clear solution, and the solution then cooled to 15° C. over 3–4 hours. The resulting precipitate was recovered by filtration, washed with toluene (100 mL), and dried to give (S)-ibuprofen N-octyl-D-glucamine salt (72.2 g, 145 mmol, 74.6% yield, MR=136°–137° C.). The toluene liquors were saved for racemization and recycle of the contained (R)-ibuprofen.

The (S)-ibuprofen N-octyl-D-glucamine salt was stirred with water (200 mL) and KOH (12 g, 214 mmol) at 50° C. for 30 minutes, and the mixture then cooled slowly to 15° C. The resulting precipitate of N-octyl-D-glucamine was recovered by filtration, washed with water (100 mL), and dried for recycle.

The aqueous filtrate was acidified with 6N HCl to pH<1. The resulting precipitate was recovered by filtration, washed with water, and dried to give (S)-ibuprofen (29.6 g, 143 mmol, 74% yield, 99.2% ee, 99.9% chemical purity).

Example 1 shows that (S)-ibuprofen may be separated from a mixture of (S)-ibuprofen and (R)-ibuprofen in high yield and enantiomeric purity in a single resolution step using N-octyl-D-glucamine as the resolving agent.

Example 2. Resolution with Recycle

Initial resolution. Racemic ibuprofen (18 g, 87 mmol) was dissolved in toluene (150 mL), and water (0.5 mL) and N-octyl-D-glucamine (12.12 g, 41 mmol) were added to the solution. The mixture was heated slowly to 75° C., forming a clear solution, and the solution then cooled to 20° C. over 3 hours. The resulting precipitate was recovered by filtration, washed with toluene (50 mL), and dried to give (S)-ibuprofen N-octyl-D-glucamine salt (14.75 g, 30 mmol, MR=136.5°–137° C., $[\alpha]_D$=−11.2° (c=0.1, MeOH), 99% ee). The toluene liquors were saved for racemization and recycle of the contained (R)-ibuprofen.

Recovery of N-octyl-D-glucamine. The (S)-ibuprofen N-octyl-D-glucamine salt was stirred with water (50 mL) and KOH (2.2 g, 39 mmol) at 45° C. for one hour, and the mixture then cooled to 15° C. The resulting precipitate was recovered by filtration, washed with water (50 mL), and dried to give N-octyl-D-glucamine (7.6 g) for recycle.

Recovery of (S)-ibuprofen. The aqueous filtrate from recovery of the N-octyl-D-glucamine was acidified with 3N HCl to pH<1. The resulting precipitate was recovered by filtration at 20° C. to give (S)-ibuprofen (5.4 g, 26 mmol, 60% yield, MR=51°–51.5° C., $[\alpha]_D$=+59.8°, 99% ee).

Further recovery of N-octyl-D-glucamine. The toluene liquors from the initial resolution were extracted with a mixture of 2N HCl (30 mL) and water (20 mL). The phases were separated and the toluene phase was washed with water (20 mL). The combined aqueous phases were made strongly basic with NaOH and then cooled; and the resulting precipitate was recovered by filtration, washed, and dried to give N-octyl-D-glucamine (5.1 g) for recycle.

Racemization. The toluene phase from the previous step was extracted with 10% aqueous NaOH (60 mL) at 60° C. The phases were separated and the aqueous phase was heated at 125° C. under pressure for 6 hours. The solution was cooled and acidified; and the resulting precipitate was recovered by filtration, washed, and dried to give racemic ibuprofen (12.2 g).

Second resolution. The racemic ibuprofen from the previous step and fresh racemic ibuprofen (5.8 g) were dissolved in toluene (150 mL), and water (0.5 mL) and N-octyl-D-glucamine (12.12 g, 41 mmol) were added to the solution. This mixture was heated to 75° C., forming a clear solution, and the solution cooled to 20° C. over 4 hours. The resulting precipitate was recovered by filtration, washed with toluene (50 mL), and dried to give (S)-ibuprofen N-octyl-D-glucamine salt (13.85 g). The (S)-ibuprofen N-octyl-D-glucamine salt was stirred with water (50 mL) and KOH (2.2 g) at 45° C. for one hour, and the mixture then cooled to 15° C. The resulting precipitate was recovered by filtration, washed with water (50 mL), and dried to give N-octyl-D-glucamine (7.3 g) for recycle. The aqueous filtrate from recovery of the N-octyl-D-glucamine was acidified with 3N HCl to pH<1. The resulting precipitate was recovered by filtration to give (S)-ibuprofen (5.35 g, 58% yield, MR=50.5°–51° C., 99% ee).

Example 2 shows that the process of Example 1 may be implemented with recycle of the N-octyl-D-glucamine and racemization and recycle of the residual (R)-ibuprofen.

Example 3. Resolution with Added Auxiliary Base

A. Racemic ibuprofen (18.03 g, 87.4 mmol), N-octyl-D-glucamine (12.12 g, 41.3 mmol), triethylamine (4.4 g, 43.5 mmol), water (0.5 mL), and toluene (150 mL) were heated to 80° C., forming a clear solution. The solution was cooled to 25° C. over 2½ hours, then cooled in an ice bath to 15° C. The resulting crystalline precipitate was recovered by filtration, washed with toluene, and dried to give (S)-ibuprofen N-octyl-D-glucamine salt (17.2 g, 78.8% yield, 94.8% ee).

B. Racemic ibuprofen (18.03 g, 87.4 mmol), N-octyl-D-glucamine (12.12 g, 41.3 mmol), triethylamine (8.6 g, 88 mmol), water (0.5 mL), and toluene (150 mL) were heated to 80° C., forming a clear solution. The solution was cooled slowly to 25° C. The resulting crystalline precipitate was recovered by filtration, washed with toluene, and dried to give (S)-ibuprofen N-octyl-D-glucamine salt (18.0 g, 82.4% yield, 86.4% ee).

Example 3 shows that (S)-ibuprofen may be separated from a mixture of (S)-ibuprofen and (R)-ibuprofen in high yield and enantiomeric purity in a single resolution step using N-octyl-D-glucamine as the resolving agent in the presence of added auxiliary base.

Example 4. Resolution using N-Methyl-D-glucamine

Racemic ibuprofen (18.03 g, 87.4 mmol), N-methyl-D-glucamine (8.2 g, 42 mmol), water (0.5 mL), and toluene (150 mL) were heated to 50° C., forming a clear solution. The solution was cooled to 20° C., then in an ice bath, and allowed to stand for 48 hours. The resulting crystalline precipitate was recovered by filtration at 20° C., washed with toluene (30 mL), and dried to give (S)-ibuprofen N-methyl-D-glucamine salt (11.9 g, 68% yield, 92% ee).

Example 4 shows that (S)-ibuprofen may be separated from a mixture of (S)-ibuprofen and (R)-ibuprofen in high yield and enantiomeric purity in a single resolution step using N-methyl-D-glucamine as the resolving agent.

Example 5. Resolution using Isopropanol as the Inert Solvent

Racemic ibuprofen (27.03, 131.03 mmol), N-octyl-D-glucamine (16.35 g, 55.73 mmol), and isopropanol (150 mL) were heated to 80° C., forming a clear solution, and the solution then cooled to 33° C. over 4 hours. The resulting precipitate was recovered by filtration, washed with isopropanol, and dried to give (S)-ibuprofen N-octyl-D-glucamine salt (23.95 g, 47.93 mmol, 73.2% yield, 99.0% ee).

Example 5 shows that (S)-ibuprofen may be separated from a mixture of (S)-ibuprofen and (R)-ibuprofen with high yield and enantiomeric purity in a single resolution step using N-octyl-D-glucamine as the resolving agent and isopropanol as the inert solvent.

The invention has been described and exemplified in specific embodiments. Those skilled in the art will understand that various changes may be made and equivalents may be substituted without departing from the invention. All such modifications are included within the claims.

We claim:

1. A process for separating (S)-ibuprofen from a mixture of (S)-ibuprofen and (R)-ibuprofen, comprising using an N-alkyl-D-glucamine as the resolving agent.

2. A process for separating (S)-ibuprofen from a mixture of (S)-ibuprofen and (R)-ibuprofen, comprising the steps of:

preparing a mixture of (S)-ibuprofen and (R)-ibuprofen and an N-alkyl-D-glucamine in an inert solvent in which the solubility of an (S)-ibuprofen N-alkyl-D-glucamine salt is significantly less than the solubility of either (R)-ibuprofen or (R)-ibuprofen N-alkyl-D-glucamine salt or (S)-ibuprofen at the temperature of crystallization, and crystallizing the (S)-ibuprofen N-alkyl-D-glucamine salt from the mixture to give a product substantially enriched in the (S)-ibuprofen N-alkyl-D-glucamine salt.

3. The process of claim 2 where the mixture of (S)-ibuprofen and (R)-ibuprofen is a racemic mixture.

4. The process of claim 2 where the N-alkyl-D-glucamine is N-octyl-D-glucamine.

5. The process of claim 2 where the N-alkyl-D-glucamine is N-methyl-D-glucamine.

6. The process of claim 2 where the N-alkyl-D-glucamine/(S)-ibuprofen molar ratio is 0.7–1.1.

7. The process of claim 6 where the N-alkyl-D-glucamine/(S)-ibuprofen molar ratio is 0.8–1.

8. The process of claim 7 where the N-alkyl-D-glucamine/(S)-ibuprofen molar ratio is 0.9–0.95.

9. The process of claim 2 where the mixture does not contain an auxiliary base.

10. The process of claim 2 where the mixture does contain an auxiliary base.

11. The process of claim 10 where the auxiliary base/total ibuprofen molar ratio in the mixture is up to about 1.

12. The process of claim 11 where the (N-alkyl-D-glucamine+auxiliary base)/total ibuprofen molar ratio in the resolution mixture is up to about 1.

13. The process of claim 2 where the inert solvent comprises a non-polar solvent.

14. The process of claim 13 where the non-polar solvent comprises toluene.

15. The process of claim 14 where the non-polar solvent comprises toluene and up to 1% water.

16. The process of claim 13 where the non-polar solvent comprises toluene and up to 10% $C_1$-$C_4$ alcohol.

17. The process of claim 2 further comprising the step of dissolving the product substantially enriched in the (S)-ibuprofen N-alkyl-D-glucamine salt in water, and cleaving the salt to give substantially pure (S)-ibuprofen.

18. An (S)-ibuprofen N-alkyl-D-glucamine salt.

19. The salt of claim 18 which is the (S)-ibuprofen N-octyl-D-glucamine salt.

* * * * *